United States Patent

Bessard et al.

[11] Patent Number: 5,821,368
[45] Date of Patent: Oct. 13, 1998

[54] METHOD FOR PREPARING PYRIMIDIN-2-YLACETIC ACID ESTERS

[75] Inventors: Yves Bessard, Sierre; Gerhard Stucky, Brig-Glis, both of Switzerland

[73] Assignee: Lonza AG, Gampel/Valais, Switzerland

[21] Appl. No.: 889,442

[22] Filed: Jul. 8, 1997

[30] Foreign Application Priority Data

Jul. 18, 1996 [CH] Switzerland .............. 1798/96

[51] Int. Cl.⁶ .............. C07D 239/34; C07D 239/26
[52] U.S. Cl. .............. 544/335; 544/319
[58] Field of Search .............. 544/335, 319

[56] References Cited

U.S. PATENT DOCUMENTS 5,322,959  6/1994  Wu .............. 560/105

FOREIGN PATENT DOCUMENTS 0353640  2/1990  European Pat. Off. .
0552759  7/1993  European Pat. Off. .
3826230  2/1990  Germany .

OTHER PUBLICATIONS

Wada, A., et al., Synthesis, Stuttgart, Germany, (Jul. 7, 1986), pp. 555–556.

*Primary Examiner*—John M. Ford
*Attorney, Agent, or Firm*—Fisher,Christen&Sabol

[57] ABSTRACT

A method for preparing pyrimidin-2-ylacetic acid esters of the general formula:

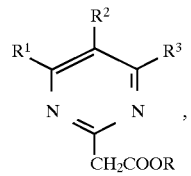

wherein R is $C_{1-6}$-alkyl, $C_{3-6}$-cycloalkyl, aryl or arylalkyl and $R^1$ to $R^3$, independently of one another, are hydrogen, $C_{1-6}$-alkyl, fluorinated $C_{1-6}$-alkyl, $C_{1-6}$-alkoxy, ($C_{1-6}$-alkoxy)-$C_{1-6}$-alkyl or ($C_{1-6}$-alkoxy)carbonyl. These esters are obtained from the corresponding 2-(halomethyl)-pyrimidine, the corresponding alcohol ROH and carbon monoxide in the presence of a palladium-phosphine complex and a base. Pyrimidin-2-ylacetic acid esters are intermediates in the preparation of herbicides.

18 Claims, No Drawings

METHOD FOR PREPARING PYRIMIDIN-2-YLACETIC ACID ESTERS

BACKGROUND OF THE INVENTION

1. Field of the Invention

The invention relates to a method for preparing substituted pyrimidin-2-ylacetic acid esters by reacting 2-(halomethyl)pyrimidines with carbon monoxide and an alcohol in the presence of a catalyst and a base. The esters which can be prepared according to the invention have the general formula:

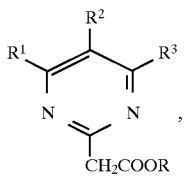

wherein:
R represents $C_{1-6}$-alkyl, $C_{3-6}$-cycloalkyl, aryl or arylalkyl, and
$R^1$ to $R^3$, independently of one another, represent hydrogen, $C_{1-6}$-alkyl, fluorinated $C_{1-6}$-alkyl, $C_{1-6}$-alkoxy, $(C_{1-6}$-alkoxy$)$-$C_{1-6}$-alkyl or $(C_{1-6}$-alkoxy$)$ carbonyl.

2. Background Art

Compounds having the structure of formula I are intermediates for the preparation of herbicides and plant growth regulators (German Published Patent Application No. 3,826,230).

A known synthesis of these compounds (with $R^1=R^3=$ alkoxy) starts from the corresponding 2-(chloromethyl) pyrimidine, which is converted with sodium cyanide into the pyrimidin-2-ylacetonitrile. The latter is reacted with alcohol/hydrogen chloride to give the imino ester hydrochloride, which is then hydrolyzed to the desired ester (German Published Patent Application No. 3,826,230). This process comprises a number of steps and produces only moderate yield; moreover, it necessitates the handling of highly toxic cyanide and corrosive hydrogen chloride.

BROAD DESCRIPTION OF THE INVENTION

An object of the invention is to provide a method which affords the desired product in only one step and with good yield. Other objects and advantages of the invention are set out herein or are obvious herefrom to one skilled in the art.

The objects and advantages of the invention are achieved by the process of the invention.

The invention involves a method for preparing pyrimidin-2-ylacetic acid esters of the general formula:

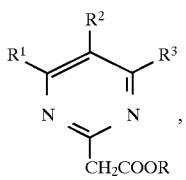

wherein R is $C_{1-6}$-alkyl, $C_{3-6}$-cycloalkyl, aryl or arylalkyl, and $R^1$ to $R^3$, independently of one another, are hydrogen, $C_{1-6}$-alkyl, fluorinated $C_{1-6}$-alkyl, $C_{1-6}$-alkoxy, $(C_{1-6}$-alkoxy$)$-$C_{1-6}$-alkyl or $(C_{1-6}$-alkoxy$)$carbonyl. It has been found that 2-(halomethyl)pyrimidines of the general formula:

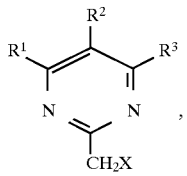

wherein $R^1$ to $R^3$ have the above-mentioned meanings and X is chlorine or bromine, react directly with carbon monoxide and an alcohol of the general formula:

$$R\text{—}OH \qquad (III),$$

wherein R has the above-mentioned meaning, in the presence of a base, with good yield, to give the desired products (I), if a palladium-phosphine complex is used as the catalyst.

DETAILED DESCRIPTION OF THE INVENTION

Herein, the term $C_{1-6}$-alkyl should be understood as referring to any linear or branched primary, secondary or tertiary alkyl groups having up to 6 carbon atoms. Correspondingly, the terms $C_{1-6}$-alkoxy and $(C_{1-6}$-alkoxy$)$ carbonyl should be understood as referring to the ether and ester functions composed of $C_{1-6}$-alkyl and oxygen, or oxygen and carbonyl, respectively, and analogously $(C_{1-6}$-alkoxy$)$-$C_{1-6}$-alkyl to the alkoxyalkyl groups formed by a hydrogen atom in $C_{1-6}$-alkyl being replaced by $C_{1-6}$-alkoxy, for example, methoxymethyl or ethoxymethyl.

Herein, the term aryl should be understood to refer, in particular, to mono- or polycyclic systems, for example, phenyl, naphthyl, biphenylyl or anthracenyl. These cyclic systems may carry one or more identical or different substituents, for example, lower alkyl groups such as methyl, halogenated alkyl groups such as trifluoromethyl, lower alkoxy groups such as methoxy, or lower alkylthio (alkanesulfanyl) or alkanesulfonyl groups such as methylthio or ethanesulfonyl. The term substituted phenyl should be understood as referring to, in particular groups such as fluorophenyl, methoxyphenyl, tolyl or trifluoromethylphenyl, the substituents preferably being in the para position. Correspondingly, the term arylalkyl should be understood as referring to the groups formed from lower alkyl groups, in particular $C_{1-6}$-alkyl, by a hydrogen atom being replaced by one of the above-defined aryl groups, for example, benzyl or phenylethyl.

The 2-(halomethyl)pyrimidines (II) serving as the starting material are known compounds or can be prepared in a manner similar to that for known compounds, for example, in accordance with the method described in European Published Patent Application No. 0552759.

The 2-(halomethyl)pyrimidines employed are preferably the 2-(chloromethyl)pyrimidines (X=Cl).

Preferentially $C_{1-4}$-alkyl esters are prepared (R=$C_{1-4}$-alkyl) according to the novel invention method, by employing, as the alcohol (III), the corresponding $C_{1-4}$-alkanol. Particularly preferred are methyl, ethyl and isopropyl esters.

Likewise, preferred is the preparation of pyrimidin-2-ylacetic acid esters (I) which are unsubstituted in position 5 of the pyrimidine ring ($R^2$=H).

Particularly preferred is the preparation of pyrimidin-2-ylacetic acid esters (I) which, in positions 4 and 6 of the pyrimidine ring ($R^1$, $R^3$), carry hydrogen, $C_{1-4}$-alkoxy groups, $(C_{1-4}$-alkoxy$)$carbonyl groups or $(C_{1-4}$-alkoxy) methyl groups.

The phosphine employed in the catalytically active palladium-phosphine complex advantageously is a tertiary phosphine, suitable examples including triarylphosphines such as triphenylphosphine or triphenylphosphine substituted by the phenyl groups, or diarylphosphines in which the third valency on the phosphorus is occupied by a different organic radical, for example, by an aliphatic chain or a metallocenyl system. Preference is given to the use of diphosphines of the general formula:

$$R^4R^5P\text{—}Q\text{—}PR^6R^7 \qquad IV$$

wherein $R^4$ to $R^7$, independently of one another, represent optionally substituted phenyl, $C_{1-6}$-alkyl or $C_{3-6}$-cycloalkyl, and Q represents a 1,1'-ferrocenediyl group or a group of the formula —[$CH_2$]$_n$—, where n is 3 or 4.

The catalytically active palladium-phosphine complex is advantageously formed in situ, palladium in finely disperse elemental form (e.g., palladium on activated carbon), a Pd(II) salt (e.g., the chloride or the acetate) or a suitable Pd(II) complex [e.g., dichloro-bis(triphenylphosphine) palladium(II)] being reacted with the phosphine. Particularly preferred are palladium(II) acetate and dichloro-bis (triphenylphosphine)palladium(II). The palladium is preferably employed in an amount of from 0.02 to 2 mol percent of Pd(II) or from 0.5 to 5 mol percent of Pd(O) (e.g., as Pd/C), in each case based on the halogen compound (II). The phosphine is advantageously employed in excess (based on Pd), preferably in an amount of from 0.2 to 10 mol percent, likewise based on the halogen compound (II).

The alcohol (III) may also serve as a solvent at the same time. If required, an additional solvent can be used. Possible additional solvents include both relatively nonpolar ones, for example, toluene or xylene, and polar ones, for example, acetonitrile, tetrahydrofuran or N,N-dimethylacetamide.

The base used is preferably a weak base selected from the group consisting of the alkali metal carbonates, the alkaline earth metal carbonates, the alkali metal salts of lower carboxylic acids, the alkaline earth metal salts of lower carboxylic acids, the alkali metal hydrogen carbonates, the alkaline earth metal hydrogen carbonates, the alkali metal (hydrogen) phosphates or the alkaline earth metal (hydrogen) phosphates. Particularly preferred are the alkali metal carbonates and the alkali metal acetates, especially sodium carbonate, potassium carbonate, sodium acetate and potassium acetate.

The reaction temperature preferably is from 80° to 250° C. The carbon monoxide pressure preferably is from 1 to 50 bar.

The reaction time depends, inter alia, on the temperature, the reactivity of the compounds used and the concentration conditions, typically being in the range of a few hours. Since excessively long reaction times may give rise to secondary reactions, the progress of the reaction is advantageously monitored by means of a suitable analytical method (e.g., GC) and the reaction is terminated once the maximum product concentration has been reached.

The following examples illustrate the implementation of the novel method of the invention.

EXAMPLE 1

Methyl 4,6-dimethoxypyrimidin-2-yl acetate
(I, R=Me, $R^1=R^3$=OMe, and $R^2$=H) respectively, and analogously ($C_{1-6}$-alkoxy)-$C_{1-6}$-alkyl to the alkoxyalkyl groups An indirectly heated (oil bath) metal autoclave was charged with 1.89 g (10 mmol) of 2-(chloromethyl)-4,6-dimethoxypyrimidine, 166 mg (0.3 mmol) of 1,1'-bis (diphenylphosphino)ferrocene, 4.5 mg (20 μmol) of palladium(II) acetate, 1.23 g (15 mmol) of sodium acetate and 40 ml of methanol. The autoclave was repeatedly purged with carbon monoxide, the carbon monoxide pressure then being raised to 15 bar and the reaction mixture being heated for 2 hours at a bath temperature of 140° C./internal temperature of 123° C. GC analysis of the reaction mixture indicated a yield of 65 percent with a conversion ratio of 100 percent. To work up the reaction mixture it was concentrated in vacuo and the residue was chromatographed on silica gel 60 with hexane/ethyl acetate (3:1). The isolated yield was 1.30 g (59 percent) of yellow oil, content (GC) 96.5 percent. Other data concerning the product was:

$^1$H NMR (CDCl$_3$) δ=5.91 (s,1 H); 3.92 (s, 6H); 3.82 (s, 2H); 3.75 (s, 3H). MS (m/z): 212 (M$^+$); 211; 183; 169; 140.

EXAMPLE 2

Ethyl 4,6-dimethoxypyrimidin-2-yl acetate
(I, R=Et, $R^1=R^3$=OMe, and $R^2$=H)

The same procedure was followed as described in Example 1, except that ethanol was used instead of methanol and 1.17 g (11 mmol) of sodium carbonate was used instead of sodium acetate. The bath temperature was 140° C., the internal temperature was 127° C. and the reaction time was 2 hours. GC analysis of the reaction mixture indicated a yield of 97 percent with a conversion ratio of 100 percent. The isolated yield was 1.90 g (82.4 percent) of yellow oil, content (GC) 98.1 percent. Other data concerning the product was:

$^1$H NMR (CDCl$_3$) δ=5.92 (s, 1H); 4.22 (q, 2H); 3.92 (s, 6H); 3.80 (s, 2H); 1.28 (t, 3H). $^{13}$C NMR (CDCl$_3$) δ=14.2 (CH$_2$CH$_3$); 45.4 (CH$_2$CO); 54.0 (OCH$_3$); 60.9 (OCH$_2$); 87.9 (CH); 163.7 (C=O); 167.7 (N=C—N); 171.6 (C—OCH$_3$). MS (m/z): 226 (M$^+$); 211; 196; 181; 153; 122.

EXAMPLE 3

Isopropyl 4,6-dimethoxypyrimidin-2-yl acetate
(I, R=i-Pr, $R^1=R^3$=OMe, and $R^2$=H)

The same procedure was followed as described in Example 2, except that isopropanol was used instead of ethanol. The bath temperature was 143° C., the internal temperature was 130° C. and the reaction time was 2 hours. GC analysis of the reaction mixture indicated a yield of 94 percent with a conversion ratio of 100 percent. The isolated yield was 1.34 g (54 percent) of yellow oil, content (GC 97 percent). Other data concerning the product was:

$^1$H NMR (CDCl$_3$), δ=5.92 (s, 1H); 5.10 (sept. 1H); 3.91 (s, 6H); 3.78 (s, 2H); 1.26 (t, 6H). $^{13}$C NMR (CDCl$_3$) δ=21.81 (CH(CH$_3$)$_2$); 45.63 (CH$_2$CO); 54.02 (OCH$_3$); 68.31 (OCH); 87.91 (C—CH—C); 163.87 (C=O); 169.22 (N=C—N); 171.56 (C—OCH$_3$). MS (m/z): 240 (M$^+$); 197; 181; 154; 125; 113.

What is claimed is:

1. A method for preparing pyrimidin-2-ylacetic acid esters of formula:

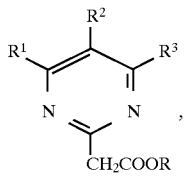

wherein R is $C_{1-6}$-alkyl, $C_{3-6}$-cycloalkyl, aryl or arylalkyl and $R^1$ to $R^3$, independently of one another, are hydrogen, $C_{1-6}$-alkyl, fluorinated $C_{1-6}$-alkyl, $C_{1-6}$-alkoxy, ($C_{1-6}$- alkoxy)-$C_{1-6}$-alkyl or ($C_{1-6}$-alkoxy)carbonyl, comprising reacting a 2-(halomethyl)pyrimidine of formula:

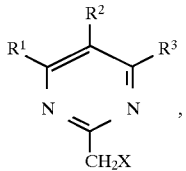   II wherein $R^1$ to $R^3$ have the above-mentioned meanings and X is chlorine or bromine, with carbon monoxide and an alcohol of formula:

R—OH   III, wherein R has the above-mentioned meaning, in the presence of a catalytically active palladium-phosphine complex and a base.

2. The method according to claim 1, wherein X is chlorine.

3. The method according to claim 2, wherein R is $C_{1-4}$-alkyl.

4. The method according to claim 3, wherein $R^2$ is hydrogen.

5. The method according to claim 4, wherein $R^1$ and $R^3$ are hydrogen, $C_{1-4}$-alkoxy, ($C_{1-4}$-alkoxy)carbonyl, or ($C_{1-4}$-alkoxy)methyl.

6. The method according to claim 5, wherein the phosphine employed in the catalytically active palladium complex is a diphosphine of formula:

$R^4R^5P$—Q—$PR^6R^7$   IV wherein $R^4$ to $R^7$, independently of one another, are phenyl, substituted phenyl, $C_{1-6}$-alkyl or $C_{3-6}$-cycloalkyl, and Q represents a 1,1'-ferrocenediyl group or a group of the formula —$[CH_2]_n$—, wherein n is 3 or 4.

7. The method according to claim 6, wherein the catalytically active palladium-phosphine complex is formed in situ from the phosphine and palladium(II) acetate or dichloro-bis(triphenylphosphine)palladium(II).

8. The method according to claim 7, wherein the base employed is a base selected from the group consisting of the alkali metal salts of lower carboxylic acids, the alkaline earth metal salts of lower carboxylic acids, the alkali metal carbonates, the alkaline earth metal carbonates, the alkali metal hydrogen carbonates, the alkaline earth metal hydrogen carbonates, the alkali metal (hydrogen) phosphates and the alkaline earth metal (hydrogen) phosphates.

9. The method according to claim 8, wherein the base employed is an alkali metal carbonate or an alkali metal acetate.

10. The method according to claim 9, wherein the base is sodium carbonate, potassium carbonate, sodium acetate or potassium acetate.

11. The method according to claim 1, wherein R is $C_{1-4}$-alkyl.

12. The method according to claim 1, wherein $R^2$ is hydrogen.

13. The method according to claim 1, wherein $R^1$ and $R^3$ are hydrogen, $C_{1-4}$-alkoxy, ($C_{1-4}$-alkoxy)carbonyl, or ($C_{1-4}$-alkoxy)methyl.

14. The method according to claim 1, wherein the phosphine employed in the catalytically active palladium complex is a diphosphine of formula:

$R^4R^5P$—Q—$PR^6R^7$   IV wherein $R^4$ to $R^7$, independently of one another, are phenyl, substituted phenyl, $C_{1-6}$-alkyl or $C_{3-6}$-cycloalkyl, and Q is a 1,1'-ferrocenediyl group or a group of the formula —$[CH_2]_n$—, wherein n is 3 or 4.

15. The method according to claim 1, wherein the catalytically active palladium-phosphine complex is formed in situ from the phosphine and palladium(II) acetate or dichloro-bis(triphenylphosphine)palladium(II).

16. The method according to claim 1, wherein the base employed is a base selected from the group consisting of the alkali metal salts of lower carboxylic acids, the alkaline earth metal salts of lower carboxylic acids, the alkali metal carbonates, the alkaline earth metal carbonates, the alkali metal hydrogen carbonates, the alkaline earth metal hydrogen carbonates, the alkali metal (hydrogen) phosphates and the alkaline earth metal (hydrogen) phosphates.

17. The method according to claim 1, wherein the base employed is an alkali metal carbonate or alkali metal acetate.

18. The method according to claim 17, wherein the base is sodium carbonate, potassium carbonate, sodium acetate or potassium acetate.

* * * * *